(12) United States Patent
Seward (10) Patent No.: US 7,127,284 B2
(45) Date of Patent: Oct. 24, 2006

(54) ELECTROPORATION MICRONEEDLE AND METHODS FOR ITS USE

(75) Inventor: Kirk Patrick Seward, Dublin, CA (US)

(73) Assignee: Mercator MedSystems, Inc., San Leandro, CA (US)

( * ) Notice: Subject to any disclaimer, the term of this patent is extended or adjusted under 35 U.S.C. 154(b) by 544 days.

(21) Appl. No.: 10/167,239

(22) Filed: Jun. 10, 2002

(65) Prior Publication Data

US 2002/0198512 A1   Dec. 26, 2002

Related U.S. Application Data

(60) Provisional application No. 60/297,418, filed on Jun. 11, 2001.

(51) Int. Cl.
*A61N 1/30* (2006.01)
*A61M 5/32* (2006.01)

(52) U.S. Cl. .......................................... 604/20; 604/272

(58) Field of Classification Search ............ 604/20–22, 604/264, 272; 606/32, 34, 41
See application file for complete search history.

(56) References Cited

U.S. PATENT DOCUMENTS

| | | | | |
|---|---|---|---|---|
| 5,273,525 | A | * | 12/1993 | Hofmann .................. 604/21 |
| 5,389,069 | A | * | 2/1995 | Weaver ..................... 604/21 |
| 5,588,961 | A | * | 12/1996 | Leone et al. .............. 604/21 |
| 5,591,139 | A | | 1/1997 | Lin et al. |
| 5,697,901 | A | | 12/1997 | Eriksson |
| 5,702,359 | A | | 12/1997 | Hofmann et al. |
| 5,807,395 | A | | 9/1998 | Mulier et al. |
| 5,823,993 | A | | 10/1998 | Lemelson |
| 5,855,801 | A | | 1/1999 | Lin et al. |
| 5,869,326 | A | | 2/1999 | Hofmann |
| 5,928,207 | A | | 7/1999 | Pisano et al. |
| 5,964,727 | A | | 10/1999 | Edwards et al. |
| 6,014,584 | A | | 1/2000 | Hofmann et al. |
| 6,077,257 | A | | 6/2000 | Edwards et al. |
| 6,090,790 | A | | 7/2000 | Eriksson |
| 6,102,887 | A | | 8/2000 | Altman |
| 6,104,952 | A | | 8/2000 | Tu et al. |
| 6,181,964 | B1 | | 1/2001 | Hofmann et al. |
| 6,233,482 | B1 | | 5/2001 | Hofmann et al. |
| 6,241,701 | B1 | | 6/2001 | Hofmann |
| 6,312,612 | B1 | | 11/2001 | Sherman et al. |
| 6,331,266 | B1 | | 12/2001 | Powell et al. |
| 6,334,856 | B1 | | 1/2002 | Allen et al. |

OTHER PUBLICATIONS

Bailey, "Local drug delivery during percutaneous coronary intervention" Current Interventional Cardiology Reports (2000) 2:349-357.

(Continued)

*Primary Examiner*—LoAn H. Thanh
(74) *Attorney, Agent, or Firm*—Townsend&Townsend& CrewLLC (57) ABSTRACT

Electroporation of cells in target tissues is performed using microneedles having integral electrode structures. In a first embodiment, a pair of electrode structures are disposed on opposite sides of a substance delivery opening on a needle or other tissue-penetrating shaft. In a second embodiment, a first electrode structure is disposed on the needle and a second electrode structure is disposed on an attached base. The electrode structures are spaced closely together and relatively low voltages are applied to achieve electroporation-enhanced substance delivery.

7 Claims, 6 Drawing Sheets

OTHER PUBLICATIONS

Chan et al., "Update on pharmacology for restenosis" Current Interventional Cardioogy Reports (2001) 3:149-155.

Stupar et al., "Silicon, parylene, and silicon/parylene micro-needles for strength and toughness" Transducers '01, 11th International Conference on Solid-State Sensors and Actuators, Munich, Germany, (Jun. 10-14, 2001) 4 pages total.

Varenne et al., "Gene therapy for coronary restenosis: A promising strategy for the new millennuim?" Current Interventional Cardiology Reports (2000) 2:309-315.

Product Brochure for "The Infiltrator®" Device Specifications, Interventional Technologies, Inc., 3574 Ruffin Road, San Diego, CA 92123, 4 pages total.

* cited by examiner

ELECTROPORATION MICRONEEDLE AND METHODS FOR ITS USE

CROSS-REFERENCES TO RELATED APPLICATIONS

This application claims the benefit of prior provisional application No. 60/297,418, filed on Jun. 11, 2001, the full disclosure of which is incorporated herein by reference.

BACKGROUND OF THE INVENTION

1. Field of the Invention

Drug and gene delivery to solid tissues is of significant medical and scientific interest. Most simply, drugs and genes can be injected into muscle, organs, and other solid tissues using a needle under pressure, typically provided by a syringe. While many small molecule drugs are adequately taken up by such straight-forward injection methods, the delivery and uptake of large molecules (such as proteins) and genes (and other nucleic acids) is often more problematic. In particular, the successful delivery of functional genes to solid tissues such that the genes are expressed can often be quite difficult.

Various methods for enhancing the delivery of genes and other large molecules have been proposed. Of particular interest to the present invention, the application of an alternating electric field across the target tissue, referred to as electroporation, has been found to be of significant benefit in enhancing expression, particularly in research settings. Such application of an alternating electric field can open pores in the cellular membranes of the target tissue, allowing functional genes and other large molecules to be delivered into the cell. The application of electroporation in experimental gene therapies has been found to substantially increase successful cell transformation.

The development of successful clinical electroporation devices has been very slow. One drawback has been the need to apply relatively high voltages to achieve the needed voltage gradients at the target cells. At present, electroporation is usually accomplished by attaching a single needle or a needle array to one pole of the electroporation power supply and attaching the other pole to another needle, needle array or surface electrode. Typically, the distance between the electrode pairs is very large, often several centimeters or larger, requiring high voltages, on the order of 1,000 volts or above, to achieve the necessary voltage gradients at the target tissue. Such high voltages can cause undesirable tissue damage. A second drawback has been the use of large arrays comprising many needles. Many patients recoil when feeling such apparatus.

For these reasons, it would be desirable to provide improved methods and apparatus for the electrically-enhanced delivery of genes and other large molecules to cells within solid target tissues. In particular, it would be desirable to provide methods and apparatus which could operate at lower voltages and/or with fewer penetrating structures to reduce the risk of tissue injury and damage. It would be further desirable to provide such electrically enhanced methods and apparatus which could be utilized in intravascular, minimally invasive, and other body locations which require miniaturized access tools. At least some of these objectives will be met by the inventions described hereinafter.

2. Description of the Background Art

Microneedles and electroporation apparatus are described in U.S. Pat. Nos. 6,334,856; 6,331,266; 6,312,612; 6,241,701; 6,233,482; 6,181,964, 6,090,790; 6,014,584; 5,928,207; 5,869,326; 5,855,801; 5,823,993; 5,702,359; 5,697,901; 5,591,139; 5,389,069; and 5,273,525. Electroporation methods are described in Varenne and Sinnaeve (2000) *Current Int. Cardiol. Reports* 2:309. The fabrication of silicon and paylene microneedles is described in Stupar and Pisano (2001) Transducers '01, 11th Int'l Conference on Solid-State Sensors and Actuators, Munich, Germany, Jun. 10–14, 2001. The full disclosures of each of these prior patents and publications are incorporated herein by reference.

BRIEF SUMMARY OF THE INVENTION

The present invention provides improved methods and apparatus for the electrically-enhanced delivery of substances to cells in solid target tissues. The application of an alternating electric field provides "electroporation" of the individual cells in the target tissue, which in turn causes a temporary opening of pores in the membranes of those cells. Such pores enhance the intracellular delivery of genes, nucleic acids, proteins, and other large molecules, which in the absence of electroporation might have a very difficult time entering into the cells. While the present invention is particularly useful for the delivery of such large molecules, it will also be useful for the delivery of small molecule drugs, typically having molecular weights below 2 kD, which for a variety of reasons, might have difficulty entering particular target cells.

The present invention relies on the use of injection apparatus comprising a shaft, such as a needle, having a substance delivery lumen therein. At least one electrode structure is disposed on the shaft near a delivery opening in the shaft which communicates with the lumen. A second electrode structure is located close to the first electrode structure, either on the shaft or on a base or other structure attached to the shaft. The two electrode structures (and optionally further electrode structures) will be separated by very small distances, as described in more detail below, which spacings have the benefit of providing relatively high voltage gradients at the cellular level achieved by the application by relatively low voltages. Usually, to achieve such close spacings, the shaft and the electrode structures themselves will also be very small, as described in more detail below.

The use of such small injection apparatus has further advantages. For example, the present invention can utilize very short needles or other shaft structures, to achieve relatively shallow epidermal injections without penetrating deep enough for nerve reception. Additionally, such small injection structures can be incorporated into catheters and other devices intended for intravascular and minimally invasive access. Thus, genes, large molecule drugs, and other substances can be delivered from within a blood vessel, other body lumen, hollow body organ, or variety of other internal anatomical spaces. The ability to locally deliver genes and other drugs with very high efficiencies is a significant advantage.

Thus, in a first aspect of the present invention, methods for delivering a substance to solid tissue comprise penetrating a shaft into the solid tissue. The substance is then delivered through the shaft, typically through an internal lumen in the shaft, to a target site in the solid tissue. An electric field, typically an alternating electric field at a voltage and frequency-selected to deliver a desired voltage gradient to the cells in target tissue, is then applied to the target site through an electrode structure on the shaft. In a first embodiment, the electrode structure may comprise first and second electrode structures on the shaft connected to opposite poles of an electroporation power supply to induce the alternating electric field immediately adjacent to an outlet port of the substance delivery lumen. In an alternative embodiment, at least one electrode structure will be disposed near the substance delivery lumen outlet on the shaft and a second electrode structure will be disposed nearby, for example on a base structure attached near a proximal end of the shaft.

In all cases, it will be desirable that the spaced-apart electrode structures which apply the alternating electric field be positioned relatively close to each other, typically being no further apart than 2 mm, usually no further apart than 1 mm, and usually being in the range from 10 µm to 1 mm, preferably in the range from 50 µm to 750 µm, and most preferably in the range from 100 µm to 500 µm. Usually, the electrode structures will have relatively small exposed areas, typically being in the range from 0.0001 $mm^2$ to 4 $mm^2$, usually being in the range from 0.001 $mm^2$ to 2 $mm^2$, and preferably being in the range from 0.01 $mm^2$ to 1 $mm^2$.

In a second aspect of the present, electroporation apparatus comprises a base, a shaft, a first electrode structure, and a second electrode structure. The shaft has a distal end, a proximal end, and a substance-delivery lumen extending from a proximal location to an opening at a distal location on the shaft. The shaft will be adapted to penetrate tissue and thus may have a tissue-penetrating distal tip or may be combined with a separate stylet or other instrument to facilitate tissue penetration. The shaft may have any cross-sectional shape, typically being circular, but alternatively having a square cross-section, rectangular cross-section, ovoid cross-section, polygonal cross-section, irregular cross-section, or the like. The width of the shaft (or diameter in the case of circular cross-sections) will preferably be small, usually being in the range from 10 µm to 1 mm, preferably from 50 µm to 500 µm, and more preferably from 100 µm to 200 µm. Such small width shafts minimize patient trauma and are well-suited for use with the small electrode structures and electrode spacings of the present invention, as discussed in more detail below.

The shafts may be formed from any material having adequate mechanical characteristics to permit tissue penetration. Thus, the shafts may be formed from metals, such as stainless steel, polymers, semi-conductor materials, or the like. In the case of metal shafts, it may be necessary to insulate all or a portion of the exterior of the shaft to isolate the electrode structures, as described in more detail below. A presently preferred electrode structure is composed at least in part from parylene and may be fabricated as disclosed in co-pending application Ser. No. 09/877,653, having common inventorship with the present application, the full disclosure of which is incorporated herein by reference. Other suitable fabrication techniques for microneedles are described in Stupar and Pisano (2001) cited above and incorporated herein by reference. The fabrication of stainless steel microtubes suitable for use as shafts in the present invention is well-described in the medical, technical, and patent literature.

The electroporation apparatus of the present invention will usually, although not necessarily, employ relatively short shaft lengths. In general, shafts useful in the present invention may have a length in the range from 0.1 mm to 10 mm, usually from 0.2 mm to 5 mm, and preferably from 0.5 mm to 2 mm. The use of relatively short shafts (or shafts having a flange or other structure which prevent tissue penetration to some maximum depth) are advantageous since they can limit tissue penetration and substance delivery to a relatively shallow depth, typically either limited to the epidermal layer or the epidermal layer and just below that layer. In particular, such shallow insertion can avoid penetration into the nerve beds of the patient.

The first electrode structure will be disposed on the shaft near the opening at the distal location. The second electrode structure may be disposed on the shaft near the distal location, usually on a side of the opening opposite to that of the first electrode structure. Alternatively, the second electrode structure may be disposed on the base in such a way that it will engage the tissue when the shaft is penetrated into the tissue. The location of the second electrode structure on the shaft will often be employed with relatively short shaft lengths so that the first electrode structure and second electrode structure remains spaced-apart within the exemplary and preferred ranges set forth above.

When both the first and second electrodes are structures are disposed on the shaft, they will typically have exposed electrode areas within the ranges set forth above, typically having identical areas. When the second electrode structure is disposed on the base, it may have a larger electrode area, typically being in the range from 0.01 $mm^2$ to 100 $mm^2$, preferably from 0.1 mm to 100 $mm^2$, preferably from 0.1 $mm^2$ ro 10 $mm^2$, and most preferably from 0.5 $mm^1$ to 5 $mm^2$.

The base structure will typically serve as a handle or other manipulation device for the shaft. For example, the base may comprise a syringe which is attached to the shaft to allow for pressurized delivery of the substance through the substance-delivery lumen. Alternatively, the base may comprise a catheter, such as an intravascular catheter, for positioning the shaft within the vasculature for drug delivery. Alternatively, the base may comprise a simple plate or other structure. In some instances, the base may serve as an anchor for removable attachment of the shaft to a separate device, such as a catheter, syringe, substance delivery tubing, or the like. Additionally, the base will usually provide for permanent or removable attachment of the wires or cables needed to deliver the alternating current to the electrode structures in the apparatus.

As discussed above, the electrode structures shall be electrically isolated from each other as well as from other conductive elements which would interfere with the desired current flow. In the case of parylene and other electrically non-conductive shaft materials, there will be no problem in forming the electrode structures directly over the shaft, e.g., by various deposition or plating processes. In the case of stainless steel and other electrically conductive shaft materials, it will be necessary to provide for an intermediate insulating layer between the shaft and the electrode structures that are formed thereover. The ability to form electrodes and electrical current conductors over conductive and insulating materials is well-known in the art, particularly in the art of making semi-conductor devices, printed circuit boards, and the like.

Apparatus of the present invention may further comprise an alternating current power supply adapted to deliver electroporation current to the electrode structures at a desired voltage and frequency, typically selected to deliver electroporation current to the electrodes at a voltage in the range from 1 V to 30 kV. The particular voltage will depend at least in part on the spacing between the first and second electrode structures. The frequency will typically be in the range from 10 Hz to $10^7$ Hz, usually from $10^4$ Hz to $10^6$ Hz. Suitable voltages for exemplary electrode spacings are set forth in Table 1 below.

TABLE 1

| Electrode Spacing | Voltage |
|---|---|
| 10 μm | 1–30 V |
| 100 μm | 10–300 V |
| 500 μm | 50–1500 V |
| 1 mm | 100–3000 V |

DETAILED DESCRIPTION OF THE INVENTION

Figure 1:
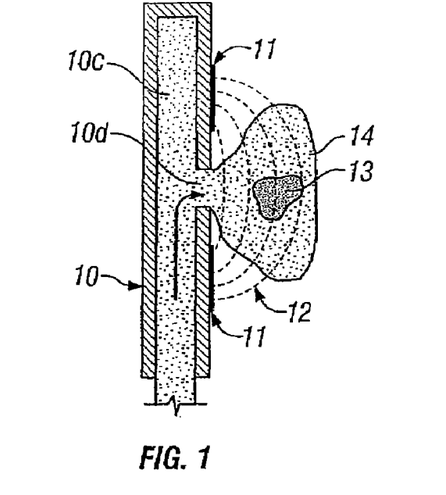
FIGS. 1 and 1A illustrate a microneedle having a pair of spaced-apart electrode structures located on opposite sides of a substance-delivery opening on a shaft.
Figure 1A:
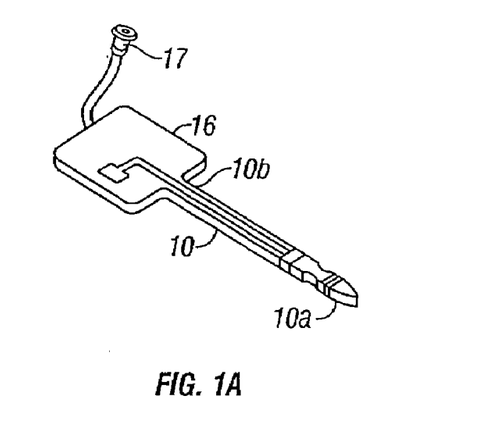

A first exemplary electroporation apparatus constructed in accordance with the principles of the present invention is illustrated in FIGS. 1 and 1A. The apparatus comprises a shaft 10 having a distal end 10a and proximal end 10b attached to a base 16 at its proximal end. The apparatus of FIGS. 1 and 1A may be formed by vapor deposition of a material into a mold or by chemical etching of a material. Suitable materials include metals, polymers, and semi-conductors Specific methods for fabricating apparatus as illustrated in FIGS. 1 and 1A are described in copending application Ser. No. 09/877,653, the full disclosure of which has previously been incorporated by reference.

The shaft 10 has a substance-delivery lumen 10c which terminates in an opening 10d in the wall of the shaft. The lumen 10c is connected to a luer or other conventional fitting 17 which permits connection of the lumen 10c to a conventional pressurized-delivery device, such as a syringe, pump, or the like. Thus, a liquid formulation carrying the substance of interest may be delivered through opening 10d as indicated by the arrow in FIG. 1. The fluid will thus pass outwardly into a region 14 surrounding a plurality of cells 13 (shown much larger than scale).

In order to enhance uptake of the substance, which may be a gene, other nucleic acid, protein or other large molecule, a small molecule drug, or the like, an electric field 12 is established between electrodes 11 spaced-apart on opposite sides of the opening 10d. The voltage, frequency, and other electrical field parameters will be selected primarily based on the distance between the electrodes 11, as set forth in Table 1 above.

Figure 2:
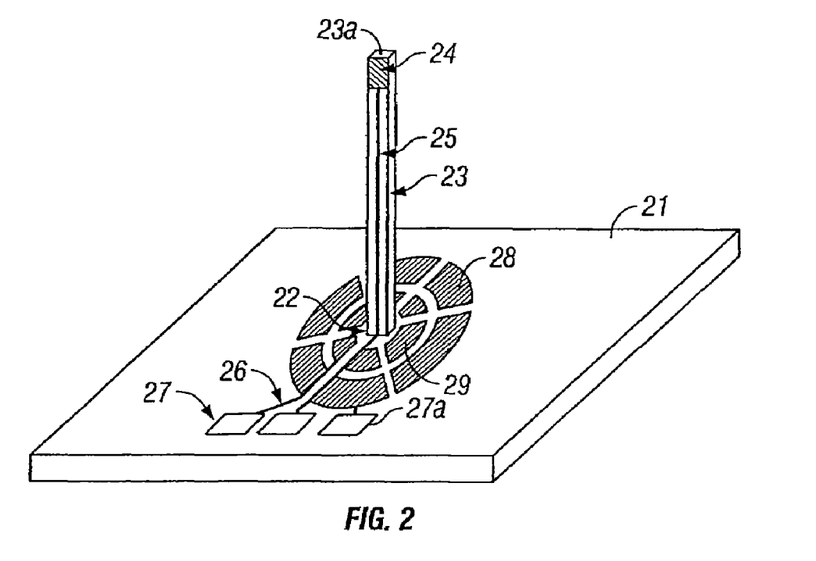
FIG. 2 illustrates an electroporation device comprising a shaft on a base having a first electrode structure on the shaft and the second electrode structure on the base.

A second exemplary electroporation apparatus constructed in accordance with the principles of the present invention is illustrated in FIG. 2. In that apparatus, a base 21 defines a ground plane having a shaft 23 projecting upwardly from a central point 22. While illustrated as a plane, the ground plane need not be "planar" or flat and instead may be curved or otherwise contoured for any particular use. The shaft 23 may be permanently affixed to the base or may be removable and/or replaceable. Additionally, the shaft 23 is illustrated in a perpendicular orientation relative to the base 21, but could be at a fixed or adjustable angle relative to the base.

The shaft 23 has a substance delivery lumen (not shown) with both an inlet port or fitting (not shown) and an outlet opening 23a at its distal tip. The first electrode structure 24 is also disposed at the distal tip of the shaft 23 and lies immediately adjacent to the opening 23a. The first electrode structure 24 is connected by a trace or other conductor 25 which extends down the exterior (or alternatively interior) of the shaft to the base and terminates in an attachment pad 26. The conductors 25 and 26 may be insulated to prevent tissue contact, but such insulation is not necessary.

In contrast to the embodiment of FIGS. 1 and 1A, the electroporation device of FIG. 2 includes a pair of second electrode structures 28 and 29 formed on the upper surface of base 21. The electrodes structures 28 and 29 are formed as concentric bands and are connected, respectively, to conductive pads 27 and 27a. While illustrated as being divided into six individual segments, each of the bands 28 and 29 may have a variety of particular configurations. Thus, each band and banded segment can be wired together to an electroporation power supply, wired separately to an electroporation power supply, and can be energized in a variety of geometric and timed patterns and arrangements. Moreover, the different bands and band segments can be maintained at different electrical potentials (voltages) with respect to the first electrode structure 24.

Figure 3:
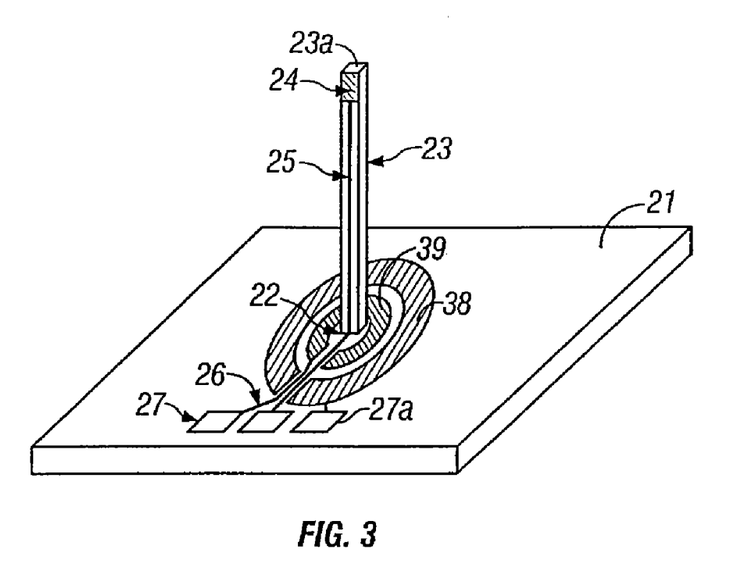
FIG. 3 is similar to FIG. 2, with an electrode structure on the base having a different configuration.

Referring now to FIG. 3, a third exemplary electroporation device constructed in accordance with the principles of the present invention is illustrated. The device of FIG. 3 is identical to that of FIG. 2, except that outer band 38 and inner band 39 are shown as continuous electrode structures rather than segmented structures. All other components are identical and have identical reference numbers. While illustrated as round, the electrode bands 38 and 39 may have other geometries, and may in some instances even cross one another. One might prefer one configuration over the other to enhance electric field uniformity in the tissue being electroporated. Various electrodes may be held at different voltage potentials to further enhance uniformity. The geometry and material of electrodes may be selected to improve the field uniformity.

Figure 4:
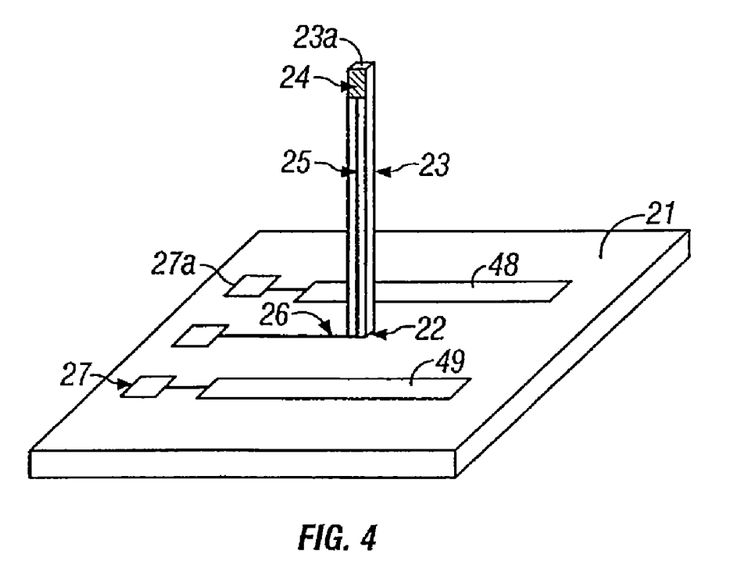
FIG. 4 is similar to FIGS. 2 and 3, with a pair of parallel electrode structures on the base.

A fourth exemplary electroporation apparatus constructed in accordance with the principles of the present invention is illustrated in FIG. 4. The apparatus of FIG. 4 is similar to that of FIGS. 2 and 3, except that the second electrode structure on base 21 comprises a pair of parallel electrode strips 48 and 49 instead of concentric electrode ring structures. All other components in the apparatus remain the same and have the same reference numbers.

While several distinct second electrode patterns have been illustrated, it will be appreciated that a wide variety of other patterns could also be used. For example, the use of single second electrode structures may also find use. Moreover, single and multiple second electrode structures need not be disposed symmetrically about the shaft 23, and instead could be located on either side of the shaft or in other non-symmetric patterns.

Figure 5:
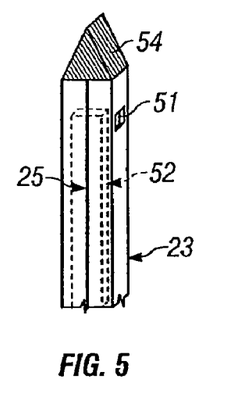
FIG. 5 illustrates a distal end of an exemplary shaft having an electrode structure at its distal tip.

Referring now to FIG. 5, the shaft 23 of the present application may be configured in many different ways. In FIG. 5, shaft 23 is shown with a sharpened distal tip having electrode 54 formed thereover. Fluid port 51 is disposed on the side of the shaft and is in fluid communication with substance-delivery lumen 52 within the shaft.

Figure 6:
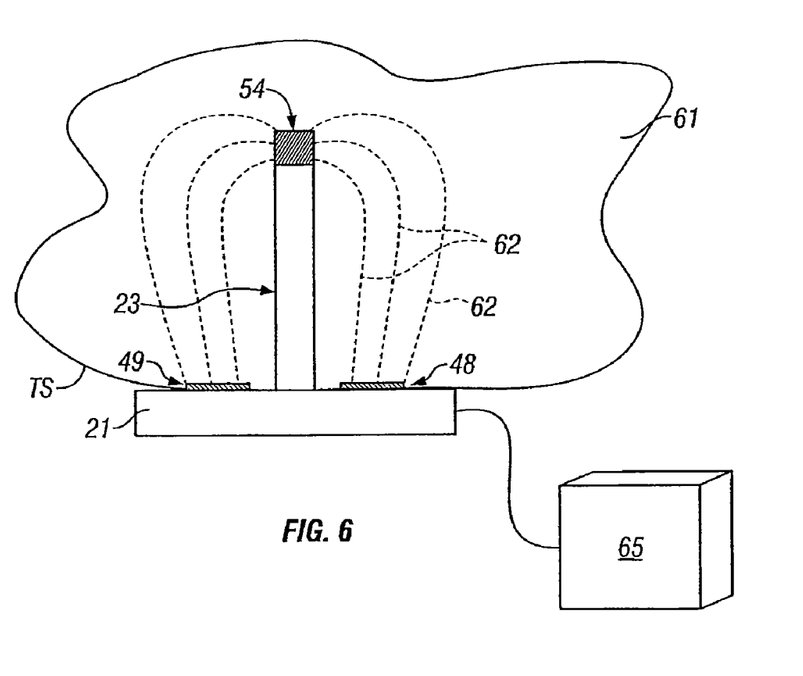
FIGS. 6 and 7 illustrate the operation of an electroporation apparatus having a first electrode structure on the shaft and a pair of second electrode structures on the base.
Figures 7, 8:
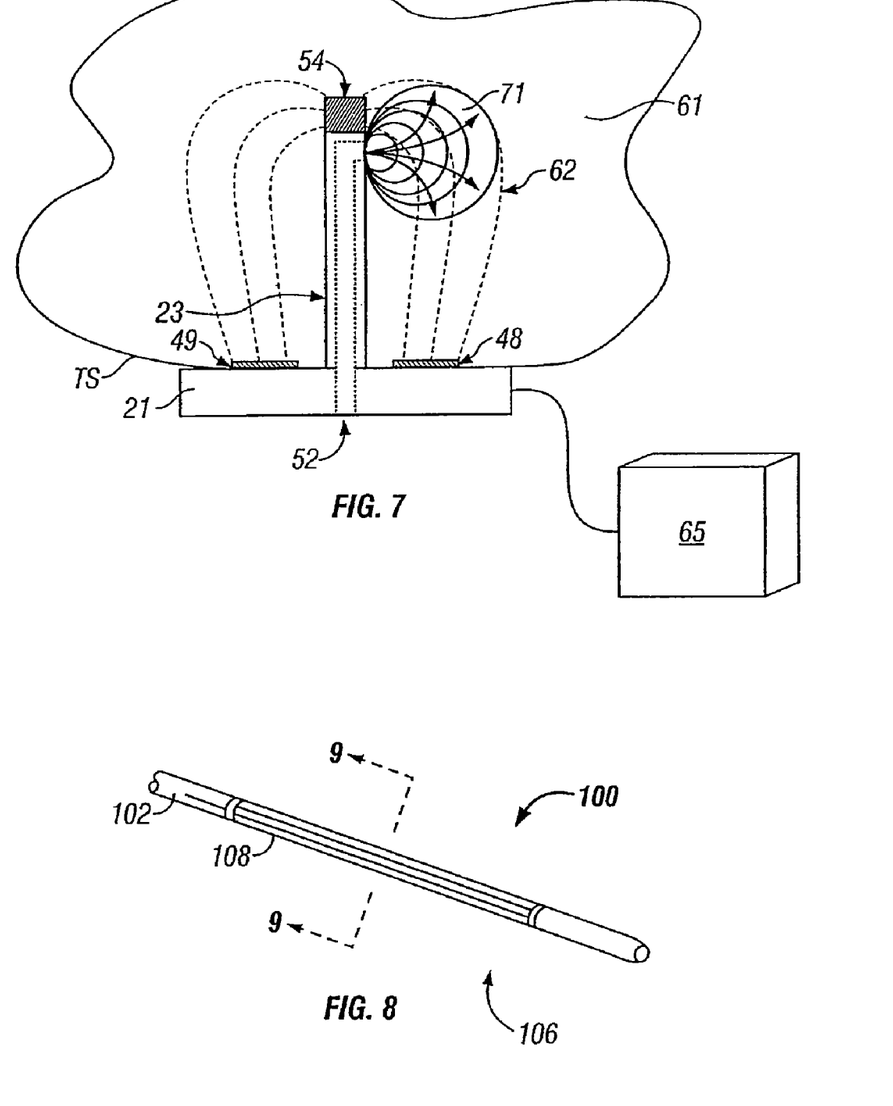
FIGS. 8 and 9 illustrate an electroporation apparatus according to the principles of the present invention where the shaft is mounted on an intravascular catheter.

Referring now to FIGS. 6 and 7, use of the apparatus of FIG. 4 having a shaft 23 as illustrated in FIG. 5 will be described. The shaft 23 is penetrated into tissue 61 so that second electrode structures 48 and 49 on base 21 engage a tissue surface TS. The tissue surface may be the patient's epidermis, i.e., external skin, or may be a surface of an internal organ or other tissue mass. The shaft 23 penetrates into the tissue 61 so that electrode 54 lies at a desired target site. An electroporation power supply 65 is connected to the electrodes 48, 49, and 54, and is energized to induce an electric field shown as broken lines 62.

As shown in FIG. 7, a liquid is delivered through lumen 52 so that it permeates through tissue outwardly in a region 71. The region 71 coincides with the electrical field being generated between first electrode structure 54 and second electrode structure 48. The electrical field enhances a cellular permeability, thus enhancing the delivery of the desired target substance to the cells.

The electroporation power supply can be a conventional power supply. The requirements and specifications of such power supplies are well described in the literature. See, for example, Neumann et al., *Electroporation and Electrofusion in Cell Biology*, Plenum Press, New York, N.Y., 1989; Chang et al., *Guide to Electroporation and Electrofusion*, Academic Press, San Diego, Calif., 1992; Jaroszeski et al., *Eletrochemotherapy, Electrogenetherapy, and Transdermal Drug Delivery: Electrically Mediated Delivery of Molecules to Cells*, Humana Press, Totowa, N.J., 2000; and Lynch and Davey, *Electrical Manipulation of Cells*, Chapman & Hall, New York, N.Y., 1996. The full disclosures of each of these publications are incorporated herein by reference.

Figure 9:
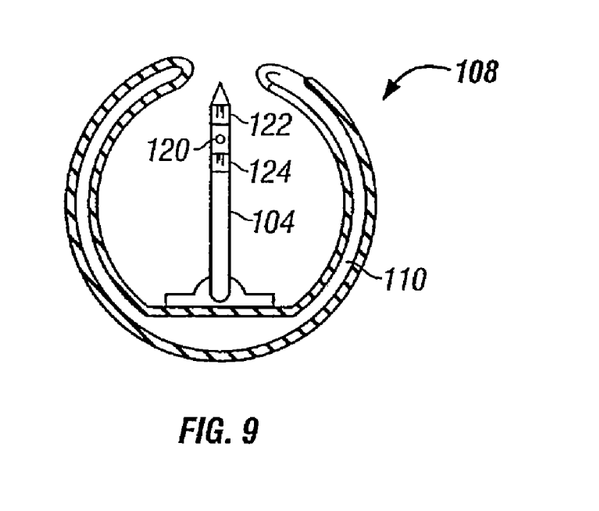

The electroporation apparatus of the present invention may be adapted for a number of particular uses, including transdermal injection, intraluminal injection, intravascular injection, injection into body organs, such as the heart, liver, kidneys, spleen, and the like. In particular, it will be desirable to incorporate the electroporation structures of the present invention into vascular and other catheters intended for use in target blood vessels and other body lumens. An exemplary catheter 100 incorporating the electroporation components of the present invention is illustrated in FIGS. 8 and 9. The catheter construction, without the electroporation components, is described in more detail in co-pending application Ser. Nos. 09/961,080, and 09/961,079, both having common inventorship with the present application, the full disclosures of which are incorporated herein by reference.

Figure 10:
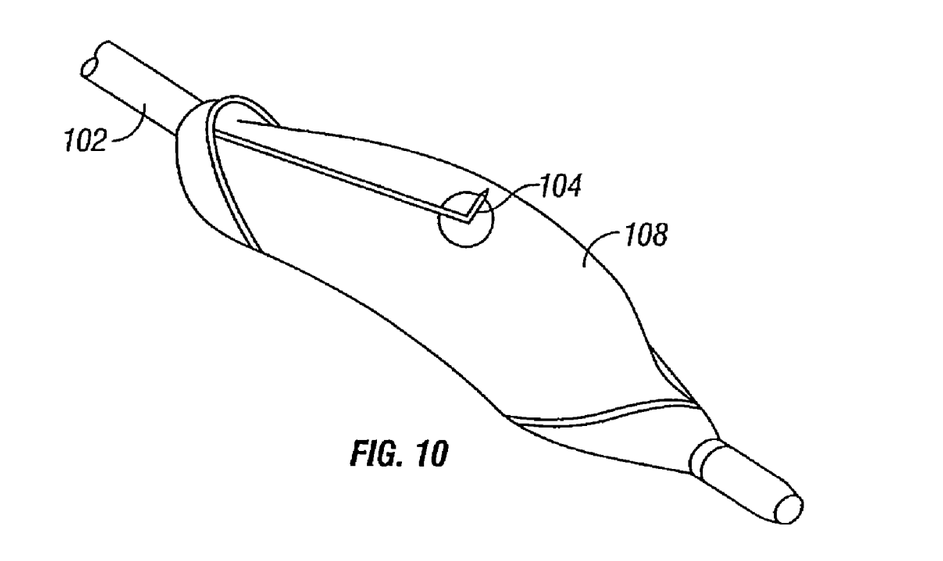
FIGS. 10 and 11 illustrate use of the apparatus of FIGS. 8 and 9 in delivering a substance into the adventitial tissue surrounding a blood vessel.
Figure 11:
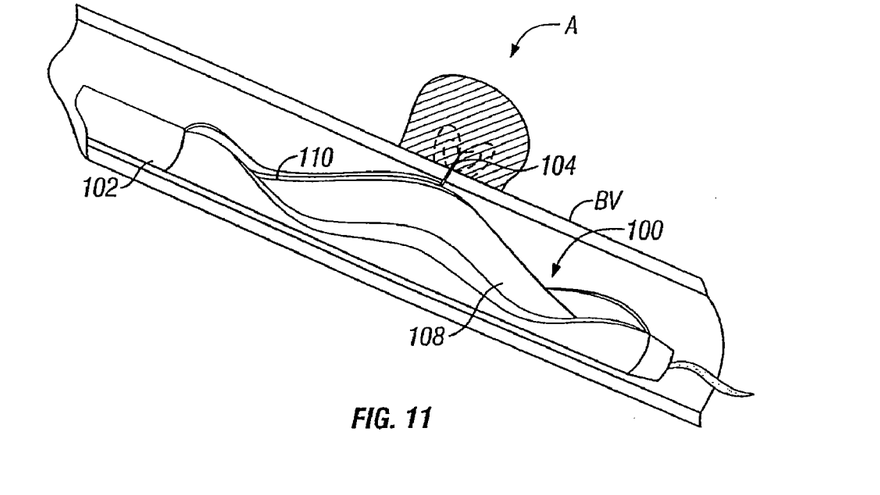

The catheter 100 comprises a catheter body 102 having a needle or other tissue-penetrating shaft 104 disposed near its distal end 106. The needle 104 is mounted on the exterior of the catheter body 102, but is normally recessed within a folded or involuted section of the catheter 108, as best shown in FIG. 9. In particular, the catheter body is involuted so that its interior 110 is in the form of a crescent or C-shaped geometry. The interior 110 at this point will be connected to an inflation source (not shown) which permits the catheter body to be expanded, as best shown in FIG. 10. It will be appreciated that the needle or other shaft structure 104 will be advanced radially outwardly so that the needle will penetrate the vascular or other luminal wall of the body lumen into which the catheter 100 has been positioned. As best shown in FIG. 11, the catheter 100 may be positioned in a blood vessel BV so that the "expanded" involuted section 108 drives the needle 104 into an adventitial region A surrounding the blood vessel. A gene, protein, or other desired substance may then be delivered into the adventitial region from a proximal portion 110 of the needle structure which is connected to a syringe or other source of the substance external to the patient. An electroporation field may then be applied between first electrode 122 and second electrode 124, as illustrated by electrode field lines in FIG. 11. Intracellular delivery of the desired substance will thus be enhanced within the cells of the adventitia.

Figure 12:
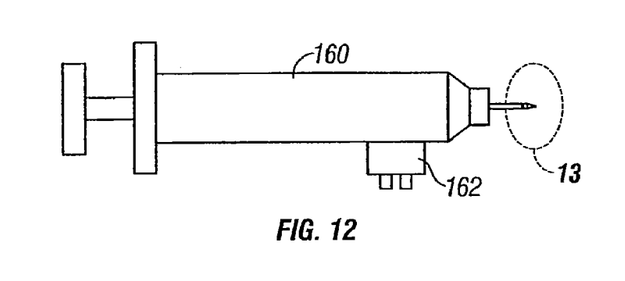
FIGS. 12 and 13 illustrate a syringe apparatus incorporating a shaft according to the principles of the present invention.
Figure 13:
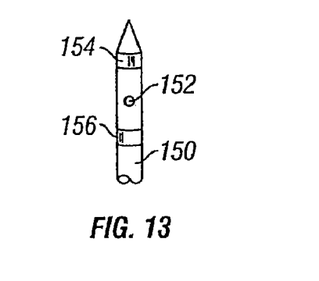

Referring now to FIGS. 12 and 13, a needle or other shaft structure 150 having a substance delivery opening 152 and first and second electrode structures 154 and 156 may be mounted directly on a syringe base 160. The syringe can deliver a desired liquid through the needle and out of the opening 152. Electrical connectors 162 positioned on the syringe barrel allow connection of the first and second electrode structures 154 and 156 to an external electroporation power supply (not shown).

While the above is a complete description of the preferred embodiments of the invention, various alternatives, modifications, and equivalents may be used. Therefore, the above description should not be taken as limiting the scope of the invention which is defined by the appended claims.

What is claimed is:

1. An electroporation apparatus comprising:
    a base;
    an elongate shaft having an axis, a distal end, a proximal end attached to the base, and a lumen extending from a proximal location to an opening at a distal location on the shaft, the distal end of the elongate shaft adapted to penetrate tissue;
    a first electrode structure disposed on the shaft near the distal location; and
    a second electrode structure disposed on the base and spaced-apart axially from the first electrode structure to establish an electric field between the first electrode structure and the second electrode structure, wherein the shaft has an outer diameter in the range from 10 μm to 1 mm and a length in the range from 0.1 mm to 10 mm.

2. The electroporation apparatus as in claim 1, wherein the first electrode structure has an exposed electrode surface area in the range from 0.001 $mm^2$ to 4 $mm^2$ and the second electrode structure has an exposed electrode surface area in the range from 0.01 $mm^2$ to 100 $mm^2$.

3. The electroporation apparatus as in claim 2, wherein the first electrode structure and the second electrode structure are spaced-apart by a distance in the range from 10 μm to 10 mm.

4. The electroporation apparatus as in claim 1, wherein the base comprises a syringe.

5. The electroporation apparatus as in claim 1, wherein the opening is through a side wall of the shaft.

6. The electroporation apparatus as in claim 1, further comprising an alternating current power supply adapted to deliver electroporation current to the electrode structures at a voltage in the range from 1 V to 30 kV.

7. The electroporation apparatus as in claim 1, further comprising a catheter body coupled with the base to urge the elongate shaft along the axis.

* * * * *